(12) United States Patent
Rubin et al.

(10) Patent No.: US 9,345,453 B2
(45) Date of Patent: May 24, 2016

(54) LUNG VENTILATION MEASUREMENTS USING ULTRASOUND

(71) Applicant: THE REGENTS OF THE UNIVERSITY OF MICHIGAN, Ann Arbor, MI (US)

(72) Inventors: Jonathan Rubin, Ann Arbor, MI (US); James Hamilton, Ann Arbor, MI (US); J. Brian Fowlkes, Ann Arbor, MI (US); Oliver D. Kripfgans, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/968,275

(22) Filed: Dec. 14, 2015

(65) Prior Publication Data

US 2016/0095580 A1   Apr. 7, 2016

Related U.S. Application Data

(62) Division of application No. 14/216,738, filed on Mar. 17, 2014, now Pat. No. 9,211,110.

(60) Provisional application No. 61/799,484, filed on Mar. 15, 2013.

(51) Int. Cl.
*A61B 8/00* (2006.01)
*A61B 8/08* (2006.01)

(52) U.S. Cl.
CPC . *A61B 8/485* (2013.01); *A61B 8/08* (2013.01); *A61B 8/461* (2013.01); *A61B 8/483* (2013.01); *A61B 8/5223* (2013.01)

(58) Field of Classification Search
CPC ........ A61B 8/08; A61B 8/0858; A61B 8/483; A61B 8/485; A61B 8/5223; A61B 8/5253
See application file for complete search history.

(56) References Cited

U.S. PATENT DOCUMENTS

| | | |
|---|---|---|
| 3,823,708 A | 7/1974 | Lawhorn |
| 3,861,387 A | 1/1975 | Lawhorn et al. |
| 3,882,853 A | 5/1975 | Gofman et al. |
| 5,722,412 A | 3/1998 | Pflugrath et al. |
| 5,817,024 A | 10/1998 | Ogle et al. |
| 5,893,363 A | 4/1999 | Little et al. |
| 6,068,602 A | 5/2000 | Tham et al. |
| 6,135,961 A | 10/2000 | Pflugrath et al. |

(Continued)

OTHER PUBLICATIONS

Bell et al., "High-frequency ventilation compared to conventional positive-pressure ventilation in the treatment of hyaline membrane disease in primates," Crit Care Med. 12(9):764-768 (1984).

(Continued)

*Primary Examiner* — Mark Remaly
(74) *Attorney, Agent, or Firm* — Marshall, Gerstein & Borun LLP

(57) ABSTRACT

An ultrasound-based system determines dynamic strain measurements over a surface using ultrasound speckle analysis that allows for accurate measurement of surface area displacement. The system additionally determines an approximate displacement along a third axis, the z-axis. From these, an estimation of a local volume change is determined. In this way, a volume change can be determined for the lung or any other region of interest.

11 Claims, 7 Drawing Sheets

(56) References Cited

U.S. PATENT DOCUMENTS

| | | |
|---|---|---|
| 6,203,498 B1 | 3/2001 | Bunce et al. |
| 6,325,759 B1 | 12/2001 | Pelissier |
| D456,509 S | 4/2002 | Schultz |
| 6,364,839 B1 | 4/2002 | Little et al. |
| 6,371,918 B1 | 4/2002 | Bunce |
| 6,383,139 B1 | 5/2002 | Hwang et al. |
| 6,416,475 B1 | 7/2002 | Hwang et al. |
| D461,895 S | 8/2002 | Barnes et al. |
| 6,447,451 B1 | 9/2002 | Wing et al. |
| 6,471,651 B1 | 10/2002 | Hwang et al. |
| D468,433 S | 1/2003 | Wagner et al. |
| D471,281 S | 3/2003 | Baura et al. |
| D475,138 S | 5/2003 | Baura et al. |
| 6,558,326 B2 | 5/2003 | Pelissier |
| 6,561,986 B2 | 5/2003 | Baura et al. |
| 6,569,101 B2 | 5/2003 | Quistgaard et al. |
| 6,575,908 B2 | 6/2003 | Barnes et al. |
| 6,602,201 B1 | 8/2003 | Hepp et al. |
| 6,604,630 B1 | 8/2003 | Cabatic et al. |
| 6,636,754 B1 | 10/2003 | Baura et al. |
| 6,648,826 B2 | 11/2003 | Little et al. |
| 6,817,982 B2 | 11/2004 | Fritz et al. |
| 6,835,177 B2 | 12/2004 | Fritz et al. |
| 6,846,288 B2 | 1/2005 | Nagar et al. |
| 6,851,392 B2 | 2/2005 | Zan et al. |
| 6,911,008 B2 | 6/2005 | Pelissier et al. |
| D509,900 S | 9/2005 | Barnes et al. |
| 6,962,566 B2 | 11/2005 | Quistgaard et al. |
| 6,979,292 B2 | 12/2005 | Kanayama et al. |
| 6,984,284 B2 | 1/2006 | Yin et al. |
| D518,574 S | 4/2006 | Chaggares |
| D520,139 S | 5/2006 | Chaggares |
| D520,140 S | 5/2006 | Chaggares |
| 7,043,293 B1 | 5/2006 | Baura |
| 7,052,460 B2 | 5/2006 | Liu et al. |
| 7,068,867 B2 | 6/2006 | Adoram et al. |
| D525,363 S | 7/2006 | Chaggares |
| 7,072,706 B2 | 7/2006 | Baumgardner et al. |
| D531,316 S | 10/2006 | Chaggares |
| 7,133,713 B2 | 11/2006 | Zan |
| 7,149,576 B1 | 12/2006 | Baura et al. |
| 7,169,108 B2 | 1/2007 | Little et al. |
| D538,432 S | 3/2007 | Diener et al. |
| D541,942 S | 5/2007 | Hirson et al. |
| 7,214,107 B2 | 5/2007 | Powell et al. |
| D544,962 S | 6/2007 | Diener et al. |
| 7,230,368 B2 | 6/2007 | Lukacs et al. |
| 7,251,524 B1 | 7/2007 | Hepp et al. |
| 7,255,678 B2 | 8/2007 | Mehi et al. |
| 7,274,325 B2 | 9/2007 | Fattah et al. |
| D558,351 S | 12/2007 | Diener et al. |
| D559,390 S | 1/2008 | Diener et al. |
| 7,426,904 B2 | 9/2008 | Zan et al. |
| 7,434,542 B2 | 10/2008 | Zan et al. |
| 7,449,640 B2 | 11/2008 | Coleman |
| D591,423 S | 4/2009 | Diener et al. |
| D592,750 S | 5/2009 | Diener et al. |
| D592,760 S | 5/2009 | Diener et al. |
| 7,534,211 B2 | 5/2009 | Hwang et al. |
| 7,549,961 B1 | 6/2009 | Hwang |
| 7,570,989 B2 | 8/2009 | Baura et al. |
| 7,588,541 B2 | 9/2009 | Floyd et al. |
| 7,591,786 B2 | 9/2009 | Holmberg et al. |
| 7,604,596 B2 | 10/2009 | Hwang et al. |
| 7,643,040 B1 | 1/2010 | Gabrielson et al. |
| D609,349 S | 2/2010 | Pelissier et al. |
| 7,686,766 B2 | 3/2010 | Quistgaard et al. |
| 7,694,814 B1 | 4/2010 | Cristobal et al. |
| 7,727,153 B2 | 6/2010 | Fritz et al. |
| 7,740,586 B2 | 6/2010 | Hwang et al. |
| 7,750,536 B2 | 7/2010 | Chaggares et al. |
| 7,798,963 B2 | 9/2010 | White et al. |
| 7,804,970 B2 | 9/2010 | Hippe et al. |
| D625,014 S | 10/2010 | Hansen et al. |
| D625,015 S | 10/2010 | Hansen et al. |
| 7,808,156 B2 | 10/2010 | Chaggares et al. |
| 7,809,400 B1 | 10/2010 | Hwang |
| 7,819,807 B2 | 10/2010 | Barnes et al. |
| 7,830,069 B2 | 11/2010 | Lukacs et al. |
| 7,841,575 B1 | 11/2010 | Sliger |
| 7,849,250 B2 | 12/2010 | Diener et al. |
| 7,867,168 B2 | 1/2011 | Little et al. |
| 7,883,276 B2 | 2/2011 | Davidson et al. |
| 7,901,358 B2 | 3/2011 | Mehi et al. |
| 7,950,971 B2 | 5/2011 | Hobet et al. |
| 7,978,461 B2 | 7/2011 | Diener et al. |
| 7,996,688 B2 | 8/2011 | Little |
| 8,016,419 B2 | 9/2011 | Zhang et al. |
| 8,052,606 B2 | 11/2011 | Barnes et al. |
| 8,066,642 B1 | 11/2011 | Little et al. |
| 8,078,256 B2 | 12/2011 | Zan |
| 8,088,070 B2 | 1/2012 | Pelissier et al. |
| 8,088,071 B2 | 1/2012 | Hwang et al. |
| 8,090,065 B2 | 1/2012 | Gabrielson et al. |
| 8,107,694 B2 | 1/2012 | Hamilton et al. |
| D654,178 S | 2/2012 | Antonio et al. |
| 8,128,050 B1 | 3/2012 | Sliger |
| 8,137,278 B2 | 3/2012 | Lundberg et al. |
| D657,361 S | 4/2012 | Goodwin et al. |
| 8,147,408 B2 | 4/2012 | Bunce et al. |
| 8,164,011 B1 | 4/2012 | Dunbar |
| 8,199,685 B2 | 6/2012 | Hwang |
| 8,213,467 B2 | 7/2012 | Little et al. |
| 8,216,146 B2 | 7/2012 | Hwang et al. |
| 8,226,562 B2 | 7/2012 | Pelissier et al. |
| 8,237,601 B2 | 8/2012 | Dunbar et al. |
| 8,275,449 B2 | 9/2012 | White et al. |
| 8,284,015 B1 | 10/2012 | Van Eyck et al. |
| 8,298,144 B2 | 10/2012 | Burcher |
| 8,310,133 B2 | 11/2012 | Brown et al. |
| 8,316,518 B2 | 11/2012 | Lukacs et al. |
| 8,317,714 B2 | 11/2012 | Hendriks et al. |
| 8,343,289 B2 | 1/2013 | Chaggares et al. |
| 8,353,833 B2 | 1/2013 | Dogra et al. |
| 8,355,554 B2 | 1/2013 | Ma et al. |
| 2001/0056235 A1 | 12/2001 | Quistgaard et al. |
| 2002/0007119 A1 | 1/2002 | Pelissier |
| 2002/0014420 A1 | 2/2002 | Schultz et al. |
| 2002/0016545 A1 | 2/2002 | Quistgaard et al. |
| 2002/0143256 A1 | 10/2002 | Wing et al. |
| 2002/0177774 A1 | 11/2002 | Hwang et al. |
| 2003/0009102 A1 | 1/2003 | Quistgaard et al. |
| 2003/0013965 A1 | 1/2003 | Quistgaard et al. |
| 2003/0013966 A1 | 1/2003 | Barnes et al. |
| 2003/0078501 A1 | 4/2003 | Barnes et al. |
| 2003/0141205 A1 | 7/2003 | Cabatic et al. |
| 2003/0163047 A1 | 8/2003 | Little et al. |
| 2003/0195418 A1 | 10/2003 | Barnes et al. |
| 2003/0199762 A1 | 10/2003 | Fritz et al. |
| 2004/0102705 A1 | 5/2004 | Zan et al. |
| 2004/0116808 A1 | 6/2004 | Fritz et al. |
| 2004/0122314 A1 | 6/2004 | Fattah et al. |
| 2004/0122319 A1 | 6/2004 | Mehi et al. |
| 2004/0122324 A1 | 6/2004 | Zan |
| 2004/0133110 A1 | 7/2004 | Little et al. |
| 2004/0138564 A1 | 7/2004 | Hwang et al. |
| 2004/0150963 A1 | 8/2004 | Holmberg et al. |
| 2004/0152982 A1 | 8/2004 | Hwang et al. |
| 2004/0193047 A1 | 9/2004 | Pelissier et al. |
| 2004/0227429 A1 | 11/2004 | Yin et al. |
| 2004/0236219 A1 | 11/2004 | Liu et al. |
| 2005/0096528 A1 | 5/2005 | Fritz et al. |
| 2005/0119555 A1 | 6/2005 | Fritz et al. |
| 2005/0131291 A1 | 6/2005 | Floyd et al. |
| 2005/0197543 A1 | 9/2005 | Zan et al. |
| 2005/0215878 A1 | 9/2005 | Zan |
| 2005/0228287 A1 | 10/2005 | Little et al. |
| 2005/0265267 A1 | 12/2005 | Hwang |
| 2005/0272183 A1 | 12/2005 | Lukacs et al. |
| 2006/0025684 A1 | 2/2006 | Quistgaard et al. |
| 2006/0058652 A1 | 3/2006 | Little |
| 2006/0058655 A1 | 3/2006 | Little |
| 2006/0241446 A1 | 10/2006 | White et al. |
| 2006/0241448 A1 | 10/2006 | Liu et al. |

(56) References Cited

U.S. PATENT DOCUMENTS

| | | |
|---|---|---|
| 2006/0241461 A1 | 10/2006 | White et al. |
| 2007/0038088 A1 | 2/2007 | Rich et al. |
| 2007/0049822 A1 | 3/2007 | Bunce et al. |
| 2007/0066898 A1 | 3/2007 | Hendriks et al. |
| 2007/0071266 A1 | 3/2007 | Little et al. |
| 2007/0085452 A1 | 4/2007 | Coleman |
| 2007/0093715 A1 | 4/2007 | Hippe et al. |
| 2007/0116373 A1 | 5/2007 | Hwang et al. |
| 2007/0121769 A1 | 5/2007 | Gabrielson et al. |
| 2007/0182287 A1 | 8/2007 | Lukacs et al. |
| 2007/0185396 A1 | 8/2007 | Zan |
| 2007/0196005 A1 | 8/2007 | White et al. |
| 2007/0205697 A1 | 9/2007 | Chaggares et al. |
| 2007/0205698 A1 | 9/2007 | Chaggares et al. |
| 2007/0222339 A1 | 9/2007 | Lukacs et al. |
| 2007/0232907 A1 | 10/2007 | Pelissier et al. |
| 2007/0232910 A1 | 10/2007 | Hwang et al. |
| 2007/0232915 A1 | 10/2007 | Pelissier et al. |
| 2007/0238954 A1 | 10/2007 | White et al. |
| 2007/0239001 A1 | 10/2007 | Mehi et al. |
| 2007/0270694 A1 | 11/2007 | Pelissier et al. |
| 2008/0015420 A1 | 1/2008 | Zan et al. |
| 2008/0015438 A1 | 1/2008 | Mehi et al. |
| 2008/0071149 A1 | 3/2008 | Rich |
| 2008/0099638 A1 | 5/2008 | Diener et al. |
| 2008/0104300 A1 | 5/2008 | Diener et al. |
| 2008/0137922 A1 | 6/2008 | Catallo et al. |
| 2008/0141107 A1 | 6/2008 | Catallo et al. |
| 2008/0183079 A1 | 7/2008 | Lundberg |
| 2008/0287789 A1 | 11/2008 | Hwang et al. |
| 2009/0043199 A1 | 2/2009 | Pelissier et al. |
| 2009/0043203 A1 | 2/2009 | Pelissier et al. |
| 2009/0043204 A1 | 2/2009 | Pelissier et al. |
| 2009/0043205 A1 | 2/2009 | Pelissier et al. |
| 2009/0069681 A1 | 3/2009 | Lundberg et al. |
| 2009/0069725 A1 | 3/2009 | Diener et al. |
| 2009/0093719 A1 | 4/2009 | Pelissier et al. |
| 2009/0108710 A1 | 4/2009 | Brown et al. |
| 2009/0198132 A1 | 8/2009 | Pelissier et al. |
| 2009/0270722 A1 | 10/2009 | Floyd et al. |
| 2009/0275835 A1 | 11/2009 | Hwang et al. |
| 2010/0049050 A1 | 2/2010 | Pelissier et al. |
| 2010/0053197 A1 | 3/2010 | Gabrielson et al. |
| 2010/0081930 A1 | 4/2010 | Dunbar |
| 2010/0090877 A1 | 4/2010 | Dunbar et al. |
| 2010/0092131 A1 | 4/2010 | Davidson et al. |
| 2010/0094132 A1 | 4/2010 | Hansen et al. |
| 2010/0121189 A1 | 5/2010 | Ma et al. |
| 2010/0121190 A1 | 5/2010 | Pagoulatos et al. |
| 2010/0121196 A1 | 5/2010 | Hwang et al. |
| 2010/0130855 A1 | 5/2010 | Lundberg et al. |
| 2010/0156244 A1 | 6/2010 | Lukacs et al. |
| 2010/0260398 A1 | 10/2010 | Ma et al. |
| 2010/0274131 A1 | 10/2010 | Barnes et al. |
| 2010/0298704 A1 | 11/2010 | Pelissier et al. |
| 2010/0298705 A1 | 11/2010 | Pelissier et al. |
| 2010/0298709 A1 | 11/2010 | Needles et al. |
| 2010/0298712 A1 | 11/2010 | Pelissier et al. |
| 2011/0021919 A1 | 1/2011 | Mehi et al. |
| 2011/0054292 A1 | 3/2011 | Hirson et al. |
| 2011/0054321 A1 | 3/2011 | White et al. |
| 2011/0057545 A1 | 3/2011 | Chaggares et al. |
| 2011/0144494 A1 | 6/2011 | Mehi et al. |
| 2011/0196237 A1 | 8/2011 | Pelissier et al. |
| 2011/0245659 A1 | 10/2011 | Ma et al. |
| 2011/0249878 A1 | 10/2011 | Pagoulatos et al. |
| 2011/0273059 A1 | 11/2011 | Brown et al. |
| 2012/0016316 A1 | 1/2012 | Zhuang et al. |
| 2012/0195161 A1 | 8/2012 | Little et al. |
| 2012/0220876 A1 | 8/2012 | Hwang |
| 2012/0226161 A1 | 9/2012 | Pelissier et al. |
| 2012/0232380 A1 | 9/2012 | Pelissier et al. |
| 2012/0243367 A1 | 9/2012 | Hwang et al. |
| 2012/0289829 A1 | 11/2012 | Barnes et al. |
| 2012/0289835 A1 | 11/2012 | Hwang |
| 2012/0296210 A1 | 11/2012 | Pelissier et al. |
| 2012/0316404 A1 | 12/2012 | Zan |
| 2013/0006110 A1 | 1/2013 | Hwang et al. |
| 2013/0010908 A1 | 1/2013 | Gabrielson et al. |

OTHER PUBLICATIONS

Boros et al., "Comparison of High-Frequency Oscillatory Ventilation and High-Frequency Jet Ventilation in Cats With Normal Lungs," Pediatr Pulmonol. 7(1):35-41 (1989).

Bunnell High-Frequency Ventilation: General Concepts. In: Donn SM, Sinha SK, eds. Neonatal respiratory care, 2nd edition. Philadelphia: Mosby, p. 222-30 (2006).

Carlon et al., "Physiologic implications of high frequency jet ventilation techniques," Crit Care Med. 11(7):508-14 (1983).

Church, et al. "Evaluation of the Threshold for Lung Hemorrhage by Diagnostic Ultrasound and a Proposed New Safety Index," Ultrasound Med Biol. 33(5):810-8 (2007).

Cools et al., "Elective high frequency oscillatory ventilation versus conventional ventilation for acute pulmonary dysfunction in preterm infants," Cochrane Database Syst Rev. (3):CD000104 (2009).

Crowley, "Antenatal corticosteroid therapy: a meta-analysis of the randomized trials, 1972 to 1994," Am J Obstet Gynecol. 173:322-35 (1995).

D'Hooge, et al. "Regional strain and strain rate measurements by cardiac ultrasound: principles, implementation and limitations," Eur J Echocardiogr. 1(3):154-70 (2000).

Doyley "Model-based elastography: a survey of approaches to the inverse elasticity problem," Phys Med Biol. 57(3):R35-73 (2012).

Galban et al., "CT-based biomarker provides unique signature for diagnosis of COPD phenotypes and disease progression," Nature Med. 18(11):1711-1715 (2012).

Garra, et al. "Elastography of Breast Lesions: Initial Clinical Results," Radiology 202:79-86 (1997).

Goddi, et al. "Real-time tissue elastography for testicular lesion assessment," Eur Radiol. 22(4):721-30 (2012).

Graustein WC. Differential Geometry. Mineola, N.Y.: Dover, 1962: 109.

Hall, et al. "In Vivo Real-Time Freehand Palpation Imaging," Ultrasound in Medicine and Biology. 29(3):427-35 (2003).

Horbar JD, Carpenter JH, Kenny M, editors. Vermont Oxford network annual database summaries 1997-2005. Burlington, VT: Vermont Oxford Network, 1998-2006.

Jackson, et al. "Effect of high-frequency ventilation on the development of alveolar edema in premature monkeys at risk for hyaline membrane disease," Am Rev Respir Dis. 143(4 Pt 1):86571 (1991).

Varghese, "Consolidation and Innovation: Driving the Global Mechanical Ventilator Markets." Published Jun. 20th, 2007. Frost and Sullivan.

Krah, "Anatomy of the mammalian lung", In: Fenn WO, Rahn H, eds. Handbook of Physiology Washington, D.C.: American Physiological Society (1964).

Lampland, et al. "The role of high-frequency ventilation in neonates: evidence-based recommendations," Clin Perinatol. 34(1):129-144 (2007).

Lichtenstein, "Ultrasound examination of the lungs in the intensive care unit," Pediatr Crit Care Med. 10(6):693-8 (2009).

Liggins, et al. "A controlled trial of antepartum glucocorticoid treatment for prevention of the respiratory distress syndrome in premature infants," Pediatrics 50(4):515-25 (1972).

Lubinski, et al. "Adaptive strain estimation using retrospective processing," IEEE Transactions on Ultrasonics, Ferroelectrics, and Frequency Control 46:97-107 (1999).

Lubinski, et al. "Speckle tracking methods for ultrasonic elasticity imaging using short time correlation," IEEE Transactions on Ultrasonics, Ferroelectrics, and Frequency Control 46:82-96 (1999).

Lucking, et al. "High-frequency ventilation versus conventional ventilation in dogs with right ventricular dysfunction," Crit Care Med 14(9):798-801 (1986).

Lyshchik, et al. "Cervical lymph node metastases: diagnosis at sonoelastography—initial experience," Radiology 243:258-67 (2007).

(56) References Cited

OTHER PUBLICATIONS

Lyshchik, et al. "Thyroid gland tumor diagnosis at US elastography," Radiology 202-211 (2005).
Meyer, et al. "Demonstration of accuracy and clinical versatility of mutual information for automatic multimodality image fusion using affine and thin-plate spline warped geometric deformations," Med Image Anal. 1(3):195-206 (1997).
Miller, "Induction of pulmonary hemorrhage in rats during diagnostic ultrasound," Ultrasound Med Biol. 38(8):1476-82 (2012).
Nikischin, et al. "A New Method to Analyze Lung Compliance When Pressure-Volume Relationship is Nonlinear," Am. J. Respir. Crit. Care Med 158(4):1052-1060 (1998).
Ophir, et al. "Elastography: a quantitative method for imaging the elasticity of biological tissues," Ultrasonic Imaging 13:111-34 (1991).
Pallwein, et al. "Real-time elastography for detecting prostate cancer: preliminary experience," BJU Int. 100(1):42-6 (2007).
Reinhardt, et al. "Registration-based estimates of local lung tissue expansion compared to xenon CT measures of specific ventilation," Med Image Anal. 12(6):752-63 (2008).
Rubin, et al. "Sonographic elasticity imaging of acute and chronic deep venous thrombosis in humans," J. Ultrasound Med., 25(9):1179-86 (2006).
Rubin, et al. "Clinical application of sonographic elasticity imaging for aging of deep venous thrombosis: preliminary findings," J Ultrasound Med. 22(5):443-8 (2003).
Rubin, et al. "Potential Use of Ultrasound Speckle Tracking for Motion Management During Radiotherapy," J Ultrasound Med 31:469-481 (2012).
Safety Group of the British Medical Ultrasound Society. Statement on the safe use, and potential hazards of diagnostic ultrasound 2000, reconfirmed Oct. 2007; Available from: <http://www.bmus.org/about-ultrasound/au-safetystatement.asp>.
Simbruner, et al. "Respiratory compliance of newborns after birth and its prognostic value for the course and outcome of respiratory distress," Respiration 43(6):414-23 (1982).
Soll, "Prophylactic natural surfactant extract for preventing morbidity and mortality in preterm infants," Cochrane Database Syst Rev. 2:CD000511 (2000).
Stefanidis, et al. "Basic principles and current applications of lung ultrasonography in the intensive care unit," Respirology 16:249-56 (2011).
Strategic Analysis of World Mechanical Ventilators. Published Mar. 5, 2005, Frost and Sullivan.
Sybrecht, et al. "Influence of posture on flow dependence of distribution of inhaled 133Xe boli," J Appl Physiol. 41(4):489-96 (1976).
Thompson, et al. "High-frequency oscillation compared with standard ventilation in pulmonary injury model," J Appl Physiol. 52(3):543-8 (1982).
U.S. Medical Ventilator Market. Published Aug. 16, 2001, Frost and Sullivan.
Wegener, et al. "Measurement of lung density by computed tomography," J Comput Assist Tomogr 2(3):263-73 (1978).
Weitzel, et al., "Feasibility of applying ultrasound strain imaging to detect renal transplant chronic allograft nephropathy," Kidney International 65:733-6 (2004).
Zhong, et al. "Measurement of regional compliance using 4DCT images for assessment of radiation treatment," Med Phys 38(3):1567-78 (2011).

LUNG VENTILATION MEASUREMENTS USING ULTRASOUND

CROSS-REFERENCE TO RELATED APPLICATION

This application is a divisional of U.S. application Ser. No. 14/216,738, filed Oct. 23, 2015, entitled "Lung Ventillation Measurements Using Ultrasound," which claims the benefit of U.S. Application No. 61/799,484, filed Mar. 15, 2013, entitled "Lung Compliance Measurement with Ultrasound," which is hereby incorporated by reference in its entirety.

BACKGROUND OF THE DISCLOSURE

1. Field of the Disclosure

The disclosure relates to measuring changes in lung volume and, more particularly, to techniques for measuring changes in lung volume using ultrasound transducers.

2. Brief Description of Related Technology

Respiratory failure is common with premature births and is a leading cause for the prevalence of ventilatory assistance among infants. For example, approximately 25% of premature neonates require mechanical ventilation due to respiratory failure. Healthcare professionals must take particular care in treating the premature neonates, because of this prevalence of the lung immaturity and the resulting harmful effects. This includes monitoring lung volume changes in neonates receiving mechanical ventilation to assess the effectiveness and safety of therapeutic treatments.

Yet, despite the respiratory problems in premature infants and neonates, presently there are no benign, reliable ways to monitor local ventilation in this population. For decades, researchers have suggested techniques for monitoring lung performance in infants, but there have been no significant breakthroughs, certainly not in terms of producing cost effective, reliable solutions. Part of the problem is the physiology involved, especially for infants. Neonates experience poor gas exchange because of atelectasis and obstructive airway disease, caused by a lack of pulmonary surfactant and immature airways. Advancements in treatment of these conditions have occurred, especially with the advent of antenatal steroid therapy and exogenous surfactant administration. But despite these treatments, large percentages of neonates still require high-frequency ventilation (HFV).

One of the problems with neonate treatment, and one of the reasons why lung volume measurement techniques are sought after is the occurrence of lung injury produced by mechanical ventilation. A condition called bronchopulmonary dysplasia (BPD) results from the effects of positive pressure ventilation and other factors required for the treatment of respiratory distress syndrome (RDS). This is not uncommon with fragile patient populations of others on ventilators, that an effective treatment option can cause other secondary conditions. In this example, the principal causes of the secondary condition (BPB) relate directly to uncertainties involved in optimizing lung volume. The issues are compounded further, however, by the myriad of different ventilators and ventilatory modes employed to ventilate infants.

As to HFV in particular, this is a type of ventilation technique that uses small tidal volumes delivered at extremely rapid rates, typically 10-20 Hz. HFV techniques have been compared and contrasted with conventional mechanical ventilation (CMV). Animal studies have suggested that HFV has fewer complications than CMV, by reducing ventilator-induced lung injury. HFV, also, has better gas exchange in the presence of air leaks; and HFV decreases oxygen requirements. However, developing a proper strategy for HFV treatment remains elusive. The technique is still highly controversial. There is no standardize criteria for optimal use of HFV; and this problem is exacerbated by the lack of accurate clinical measurements of lung volume.

SUMMARY OF THE INVENTION

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

The present application provides techniques for determining local lung strain and lung volume, and more specifically changes in lung volume, using ultrasound imaging. Ultrasound speckle tracking and strain imaging are combined with techniques for determining z-axis displacement to arrive at clinically accurate measurements of local lung volume.

In some examples, two-dimensional (2D) ultrasound speckle imaging techniques are used to determine an approximated surface area change; and the z-axis displacement is determined from separate a sensor array or other technique to independently determine physical displacement. The system may be implemented with multiple, small 2D array ultrasound transducers attached to a patient's (e.g., an infant's) chest similar to ECG leads. These will then be able to monitor local ventilation at distributed sites in real time across both lungs. These sensors could also be used in determining z-axis displacement, through a process of approximating osculating circles to the lung surface. The result is a dual-mode technique for measuring lung volume changes.

The technique may determine volume changes, between inspiration and expiration, over the entire lung or the technique may analyze a selectable portion of the lung, for example, by segmenting the ultrasound images and sensor array to a particular location.

The techniques are benign and can be applied routinely in a neonatal intensive care unit (NICU) setting. Although, more broadly, the techniques may be generalized to a monitoring method for local ventilation of any patient pool, from infant to adult. The techniques may be implemented as standalone systems or integrated with mechanical ventilation machines. The techniques may be used for diagnostic or therapeutic purposes. The techniques may be designed to provide alarm indications to attending medical personal, may be used to database patient responsiveness to treatment, may assist in diagnosis of respiratory conditions, or may provide automated instructions to a treatment apparatus.

In accordance with an example, provided is a method of determining change in the volume of a target sample, the method comprising: receiving, at an imaging processing machine, ultrasound images of a two-dimensional area corresponding to the target sample, where a first ultrasound image is taken at a first time period and a second ultrasound image is taken at a second time period after the first time period; determining, at the imaging processing machine, a change in strain value of the target sample over the two-dimensional area, wherein the strain value is determined from comparing the first ultrasound image to the second ultrasound image, wherein the first ultrasound image and the second ultrasound image are speckle-containing images; determining, at the imaging processing machine, and from the change in strain value, an xy-plane change in area of the target sample between the first time period and the second time period;

determining, at the imaging processing machine, an approximate physical z-axis displacement over the two-dimensional area by approximating a change in local curvature of the two-dimensional area between the first time period and the second time period; and determining, at the imaging processing machine, a volume displacement of the target sample from the approximate physical z-axis displacement and the change in strain value.

In accordance with another example, an apparatus comprises: an imaging processing machine having a processor and a memory, wherein the processor is configured to execute instructions that when executed cause the imaging processing machine: to receive ultrasound images of a two-dimensional area corresponding to the target sample, where a first ultrasound image is taken at a first time period and a second ultrasound image is taken at a second time period after the first time period; to determine a change in strain value of the target sample over the two-dimensional area, wherein the strain value is determined from comparing the first ultrasound image to the second ultrasound image; to determine from the change in strain value, an xy-plane change in area of the target sample between the first time period and the second time period; to determine an approximate physical z-axis displacement over the two-dimensional area by approximating a change in local curvature of the two-dimensional area between the first time period and the second time period; and to determine a volume displacement of the target sample from the approximate physical z-axis displacement and the change in strain value.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Figure 1A:
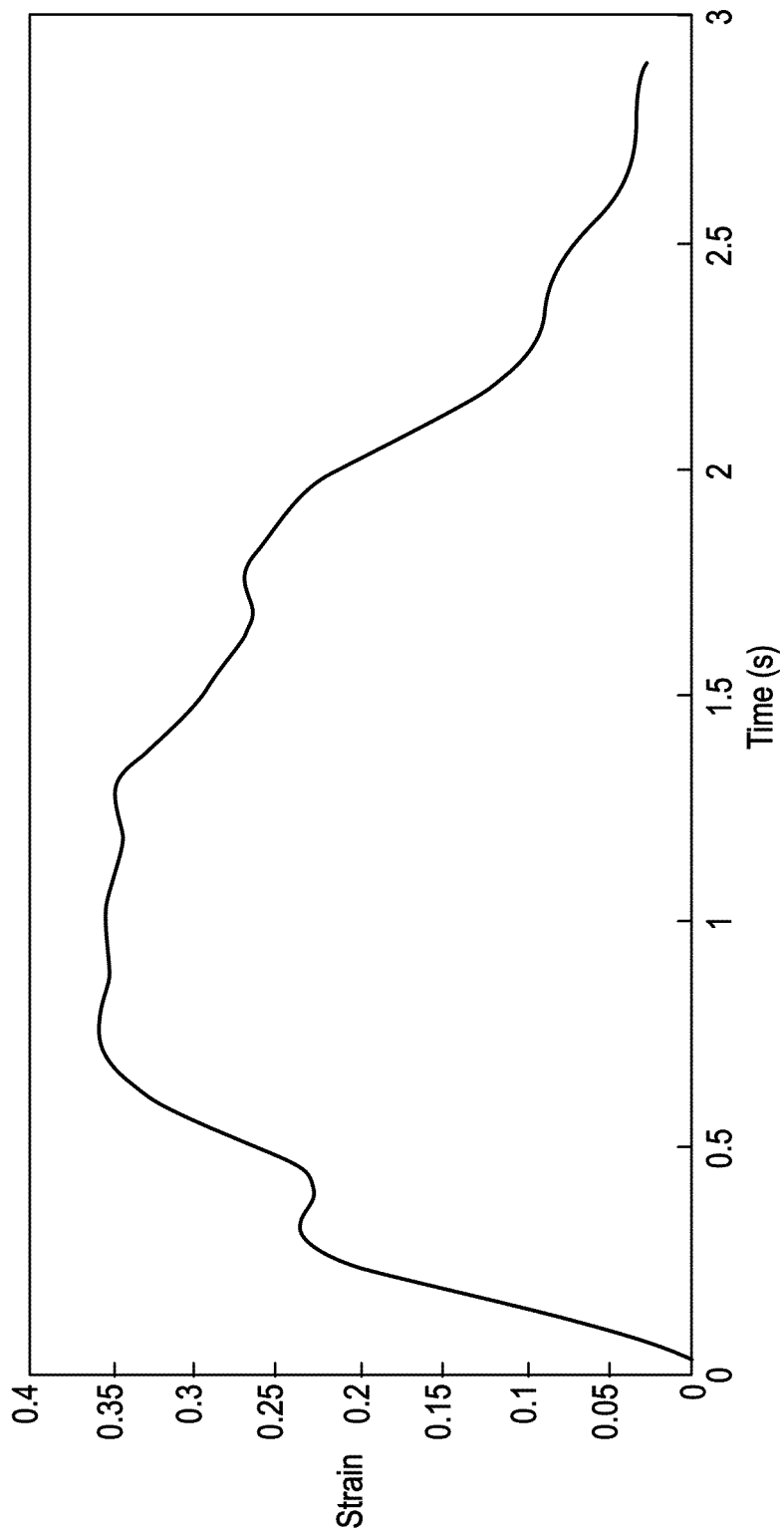
FIGS. 1A and 1B are plots of strain along two orthogonal directions obtained from a 1 dimensional transducer.

The techniques described herein rely upon ultrasound imaging to determine dynamic strain measurements of the lung surface and extend well beyond conventional strain measurement. The techniques may determine strain using ultrasound speckle analysis that allows for accurate measurement of surface area displacement. The techniques additionally approximate displacement along a third axis, the z-axis, from which an estimation of a local volume change may be achieved. Indeed, in this way, the present techniques result from an unexpected application of ultrasound strain imaging. Conventionally, ultrasound strain imaging has been used to measure only tissue hardness in multiple organ systems and disease processes, including cardiac wall and heart function, breast tumor analysis, thyroid mass assessment, deep venous thrombosis aging, lymph node metastases, renal transplant rejection, testicular tumor evaluation, and prostate tumor assessment. These applications have been attempted with varying degrees of success.

The present technique uses speckle tracking to calculate the strain in ultrasound. For example, using pattern matching techniques, we can track speckle motion in moving tissue to sub-wavelength accuracies. The tracking technology is robust and accurate; and speckle-tracking based strain imaging is available on most clinical ultrasound units. However, while strain imaging has been used to measure tissue hardness, deformation is different. Unlike tissue hardness, deformation, generally speaking, depends on a variety of external factors that will affect measurements. Stresses applied to a patient, boundary conditions for the organ, a patient's weight, organ size, etc. can all affect the deformation of an organ.

With the present techniques, we show that strain imaging may be used effectively for measuring local lung ventilation, in particular changes in lung volume. Data from the strain imaging is directly convertible to local ventilation, with positive strain data expressing expansion of the lung volume and negative strain data expressing contraction. In this way, the present techniques provide a solution to the local lung ventilation quandary, where conventional ventilators can measure the total air displacement and the pressure used to displace the gas, but cannot determine where the gas is actually going within the patient. These ventilators determine the actual impact on the lung, leaving the local distribution of the gas in the lungs unknown.

The present techniques provide a new targeted application of ultrasound speckle tracking and strain imaging, lung strain. These techniques derive from using ultrasound to solve a major problem in an organ system that is only rarely even considered a legitimate target for ultrasound. We base this on the following expression:

$$\varepsilon = \frac{\Delta l}{l}, \qquad (1)$$

where $\varepsilon$ is strain, I is an arbitrary length and $\Delta$I is the change in the length based on some deformation, such a respiratory motion. In this way, we show that strain directly correlates to deformation. We extend this linear strain to volume strain to provide relative changes in lung volume or ventilation. The result is $$\frac{\Delta V}{V} = \sum_i \varepsilon_i, \qquad (2)$$

where V is volume, $\Delta$V is change in volume, $\varepsilon_i$ is linear strain in the $i^{th}$ direction where i=x, y, or z. Thus, from Equation (2), if V is considered a small local volume element defined by the ultrasound image, then the sum of the strains in three (3) directions multiplied by the imaged volume element will give $\Delta$V.

In some examples, 2D ultrasound transducer arrays may be used to obtain a near complete map of lung ventilation. These transducer arrays may be placed around a neonate's chest, similar to ECG leads, and spaced apart based on the size of the volume area desired. In another example, 1D ultrasound transducers probes may be used to take multiple measurements at different locations on the lung. For this later example, the probes may be used to simulate a 2D array, for example, by taking a first measurement along a first one-dimensional axis and then rotating the probe to take a second measurement along an orthogonal direction, from which the orthogonal strain measurement is then determined.

Figure 5:
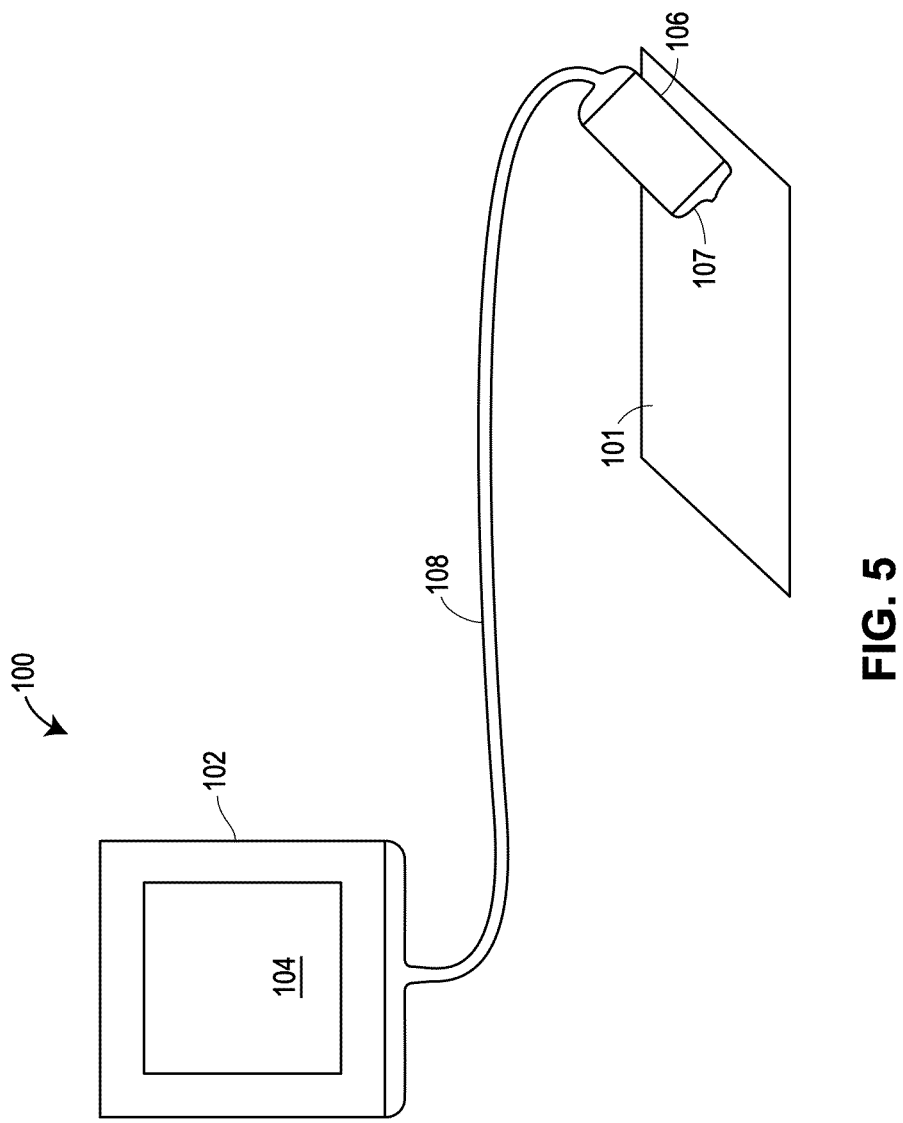
FIG. 5 illustrates an example handheld ultrasound device for determining long volume using a one-dimensional ultrasound transducer, in accordance with an example.

FIG. 5 illustrates an example handheld ultrasound device 100 that may be used to determine a change in volume of a target sample 101, such as the lung or bladder. The device 100 includes a handheld controller 102 that includes an image processing machine having a processor and embedded memory. The handheld controller 102 has a display 104 for displaying ultrasound images captured by an ultrasound transducer 106 (with scanhead 107) coupled to the controller 102 through a wired connection, such as a Universal Serial Business (USB) connector 108. In the illustrated example, the transducer 106 is a 1D transducer. However, 2D transducers and 3D ultrasound devices may be used instead. In some examples, using a USB connector allows for interchanging the transducer 106 for another transducer, 1D or 2D or what are described as 3D ultrasound or 4D ultrasound devices. In some examples, the transducer 106 may be connected wirelessly to the controller 102, using a wireless communication protocol such as any of the IEEE 802.11 standards, 802.11a, b, g, n, ac, or ad. Other example wireless communication modalities include IEEE 802.15 standard, known as "Bluetooth," and near field communication (NFC) standards used for smart devices. The controller 102 may perform the strain measurements and volume determinations discussed herein. While in other examples, the controller 102 may be part of an overall imaging processing apparatus that includes an external machine, with dedicated processor, coupled to the controller 102, wirelessly or wired, to receive preliminary ultrasound data and process that data to determine changes in strain values, across an xy-plane and the z-axis displacement.

Figure 6:
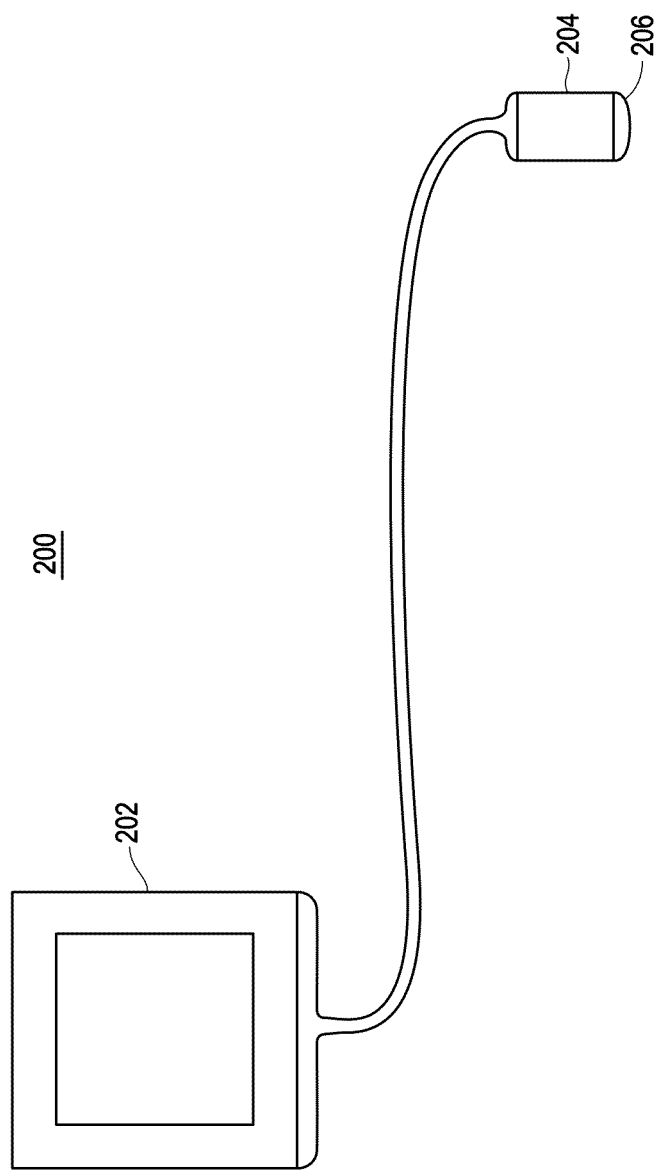
FIG. 6 illustrates an example handheld ultrasound device for determining long volume using a two-dimensional ultrasound transducer, in accordance with an example.

FIG. 6 illustrates another device 200 similar to that of the device 100, but showing a controller 202 and 2D ultrasound transducer 204, with scanhead 206. It will be appreciated that the ultrasound transducer may be implemented with a linear array, phased array, convex array, 2D array, 3D ultrasound device array, or 4D ultrasound device array, by way of example. As discussed herein, like the device 100, the device 200 can be moved over a subject to detect lung ventilation, functioning in some respects as an ultrasound stethoscope. In some example implementations of a 1D measurement, the devices herein may be used to obtain a localized one dimensional strain value. For example, a 1D ultrasound transducer may be used to collect data at two different times from which the system is able to determine a one dimensional strain value and convert that value into an indication of a localized ventilation. For example, this 1D strain/ventilation measure could be part of a binary ventilation system, that identifies whether the subject is ventilating or not, ventilating at a maximal amount or not, ventilating over a specific ventilation range, ventilating in a range of concern (too fast or two slow), etc. Indeed, while examples are described herein in reference to 2D ultrasound transducers, the techniques herein described can be implemented using 1D transducers as well. These one dimensional strain/ventilation determinations may be performed at a single location on a subject or on multiple locations on a subject. Beyond these one dimensional strain and ventilation determinations, in some examples, these 1D ultrasound transducers may be used for additionally determining volume displacements in accordance with examples discussed herein. For example, the 1D transducers can be used to collect 1D strain data along orthogonal directions and then at different times to develop a two dimensional strain data.

In some examples, the devices 100 and 200 represent example manifestations of the environment 10, the machine 12, and/or any of the machines 70-1-70-n. Indeed, any of these processing devices are included by use of the term "system" (e.g., an imaging system), as used herein. That is, it will be understood that the techniques described herein as implemented on a system may be implemented fully or partially on the devices 100 or 200, the computer 12, any of the remote computers 70-1-70-n, or any suitable other devices. And reference to operations on any of the environment 10, the machine 12, and/or any of the machines 70-1-70-n shall also include implementation on any other of the environment 10, the machine 12, and/or any of the machines 70-1-70-n.

Figure 1B:
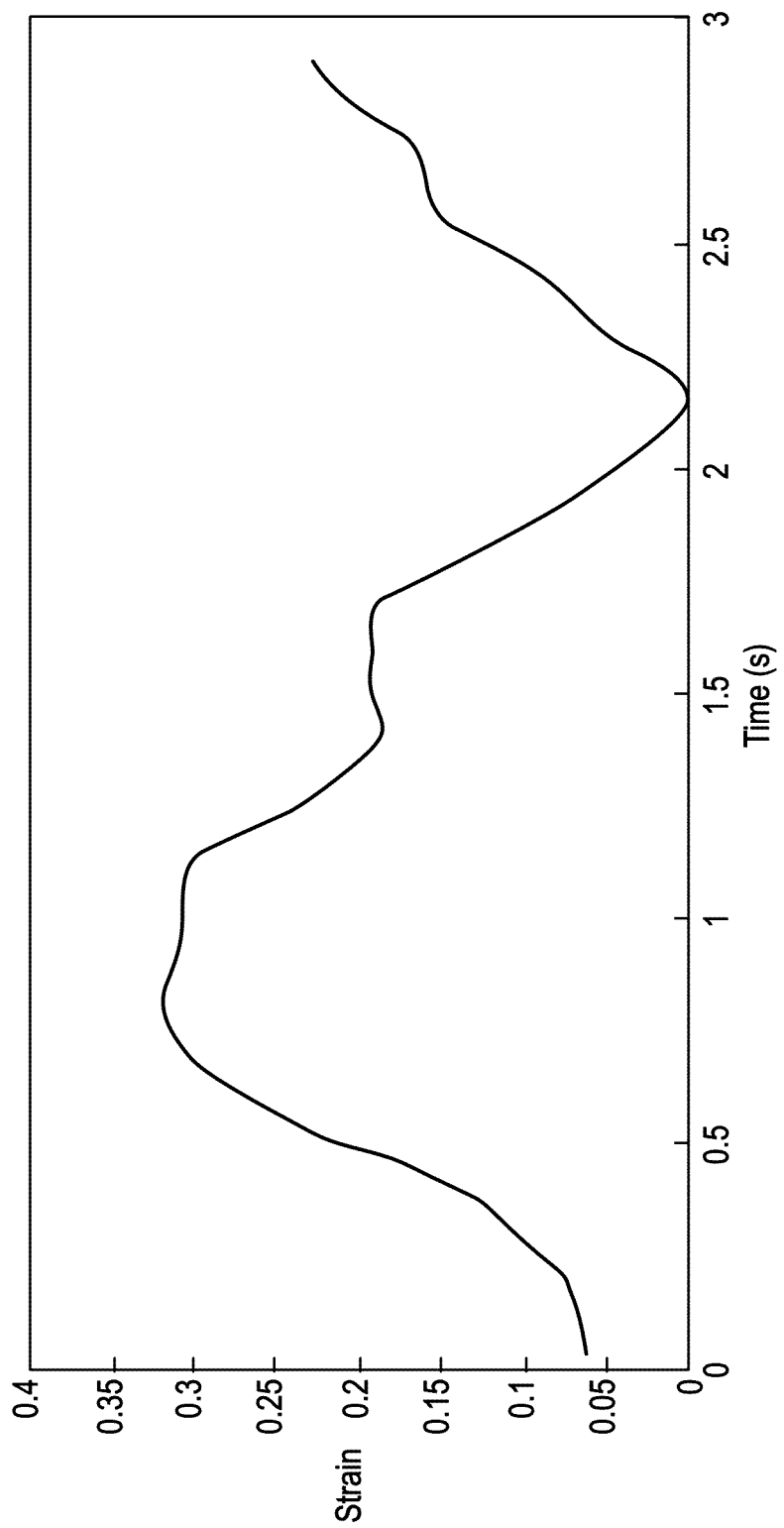

FIGS. 1A and 1B show a local map for individual breaths in a patient produced from a processed ultrasound signal from the lung surface in two-orthogonal directions (FIG. 1A and FIG. 1B), achieved by rotating a 1D ultrasound transducer, such as the transducer 106. This plot is a direct measure of local lung expansion and contraction, in the two examined directions over time. Each plot of FIGS. 1A and 1B were taken over different breaths and each oscillates in strains over about 2-3 s. The max strains were very similar, approximately 35% as shown.

In any event, whether a 1D transducer or a 2D ultrasound transducer array is used, two of the strain components from Equation (2) are obtained by tracking two orthogonal strains along the lung surface with respiration. The third component normal to the lung surface, i.e., along the z-axis, is tracked in a different manner.

Figure 2B:
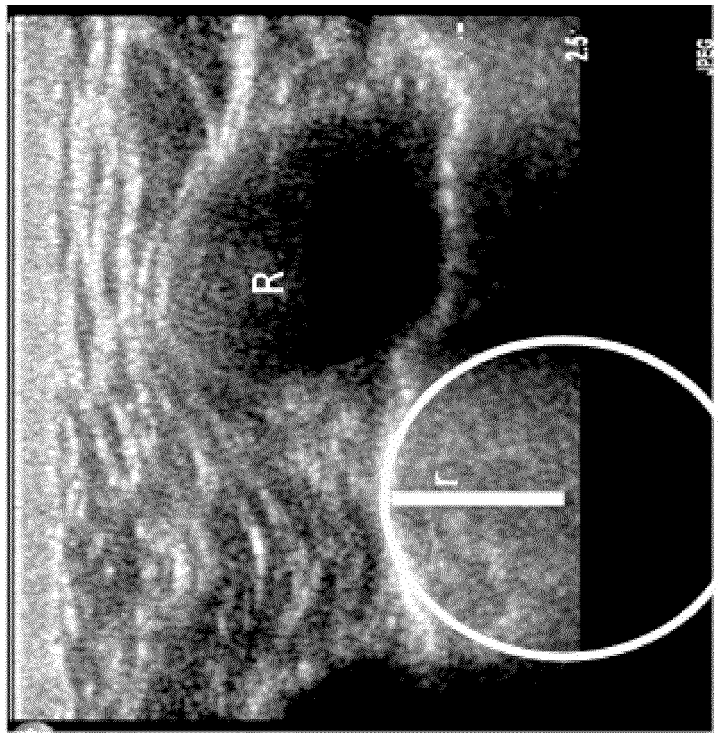
FIGS. 2A and 2B are ultrasound images of the lung during full expiration (FIG. 2A) and full inspiration (FIG. 2B), in accordance with an example.
Figure 2A:
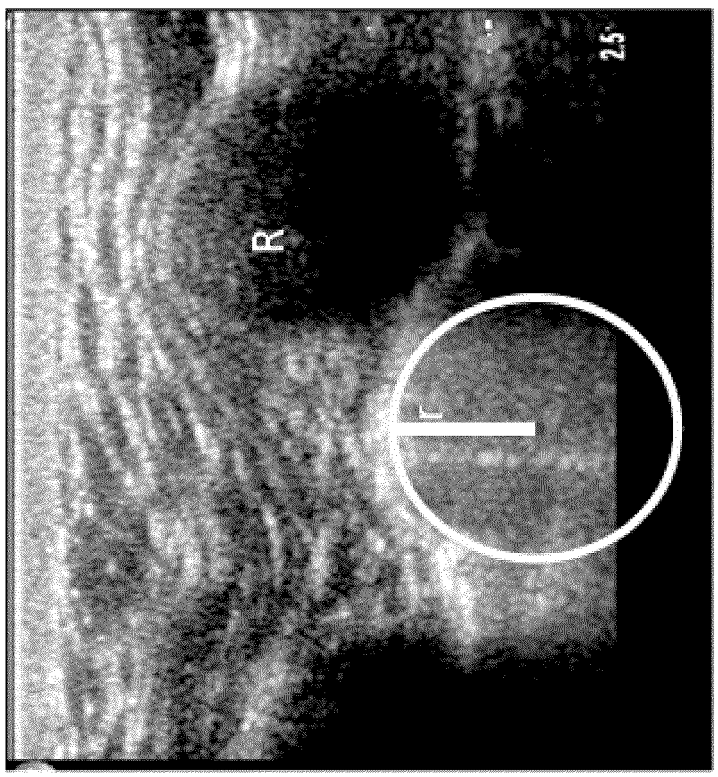

Ultrasound will not enter the air-filled lung. Yet, in some examples, a system is able to track the change in the radius of curvature of a local osculating circle centered in a sample region. The z-axis displacement may be determined different ways depending on the transducers and sensor configurations. For example, using a 1D ultrasound array (such as in the device 100 or the system 1000 implemented with a 1D array), where one may not be able to acquire orthogonal directions simultaneously along principal directions, the system may approximate the z-axis displacement by first identifying near orthogonal space curves along the lung surface by rotating the transducer similar to FIGS. 2A and 2B. The system may identify the lung surface from the ultrasound image, since it is moving and it is a total reflector of ultrasound. The system may be configured to identify the lung surface at extreme positions, for example at full inspiration and full expiration. The system may then determine osculating circles corresponding to the lung surface, e.g., by radially fitting to a portion of the lung surface, after which a z-axis displacement, e.g., a radial difference along a direction orthogonal to the portion of the lung surface, is determined. In the example of 2D ultrasound arrays, orthogonal acquisitions along principal direction can be acquired simultaneously. Therefore, space curves can be fit from the ultrasound images using continuous functions, such as cubic functions. The system can then take the second derivatives of the cubic at the center point in each direction as the curvature at that point. The system can then take the average of the two curvatures to obtain a mean curvature, which can be inverted to get the instantaneous mean radius of curvature. This example technique is similar to fitting osculating circles at the points of second order contact in the orthogonal directions and using the radii of the circles to calculate the instantaneous radii of curvature. In any event, the system can then use the temporal fluctuation of these instantaneous mean radius of curvature values around the temporal mean radius of curvature, normalized by the temporal mean radius of curvature, as an estimate of the strain in the normal direction. From this, the system is able to calculate volume strain.

From examining changes in the radius of curvature between two states, for example between inspiration (FIG. 2A) and expiration (FIG. 2B), it is possible to estimate the strain along the z-axis. In an example, FIGS. 2A and 2B may represent ultrasound images on the display 104. The illustrated example shows measurement of the radius of curvature in near full inspiration and full expiration by re-calculating the centers of the local osculating circles at those two instances. In this way, the radii of curvature of the set of osculating circles can be tracked throughout respiration. The mean value of the radii may be set as the zero strain reference point, such that the instantaneous strain in the z direction, $\varepsilon_z(t)$, is $$\varepsilon_z(t) = \frac{r(t) - \langle r \rangle}{\langle r \rangle}, \quad (3)$$

where r(t) is the instantaneous local mean radius of curvature and <r> is the temporal mean radius of curvature.

It is noted that, for a particular target, there may be different radii of curvature along different orthogonal planes. Essentially, the approximating osculating circle may be direction dependent, especially for smaller circles associated with neonates and infants. We can overcome such directional dependence, by measuring two potentially-different radii of curvatures, along different directions. In some examples, the system can estimate two curvatures, C where C=1/r. The system can average the curvatures to obtain a mean curvature or multiply them to obtain the Gaussian curvature. By inverting the mean curvature or inverting the square root of the Gaussian curvature, two estimates of a radius of curvature for the lung surface may be obtained. Using these relationships, the system can calculate the local ventilation over time by comparing the time dependency, as described herein.

Other techniques for determining changes in z-axis displacement include using an accelerometer, for example, an accelerometer embedded in the ultrasound transducer devices 106 or 204, such as embedded within the scanhead 107 and 206, respectively. The accelerometer would detect changes in movement, position, and/or pressure from, which the controller would determine z-axis displacement. In other examples, a biometric sensor, such as an activity monitory, may be embedded within the ultrasound transducer to determine z-axis displacement. In yet other examples, the accelerometer-based sensor (or other biometric sensor) may be contained within another device, such as a dedicated sensor device or a handheld or wearable "smart" device, such as smartphone or activity monitor. In some examples, the accelerometer may be within a case or housing for a handheld or wearable such device.

The accelerometer may be a single axis detection accelerometer (e.g., z-axis). In other examples, the accelerometer may detect movement in three orthogonal axes (e.g., x-, y-, and z-axes). In such examples, xy detection data may be combined with the ultrasound xy data to refine measurements of changes in area across the xy-plane. The accelerometer may be triggered to automatically perform scanning (e.g., z-axis scanning), in response to sensing the depression of the accelerometer into a subject. When embedded in an ultrasound device, that sensing may result from being depressed into the subject.

Either the accelerometer or the ultrasound transducer itself can be designed to detect the orientation of the embedded sensor and/or of the probe itself in some examples. That orientation data may be used to optimize volume measurement determinations, for example, by applying resizing and stretching on collected data. In some examples, the orientation of the accelerometer is separately controllable through the controller.

Figure 3:
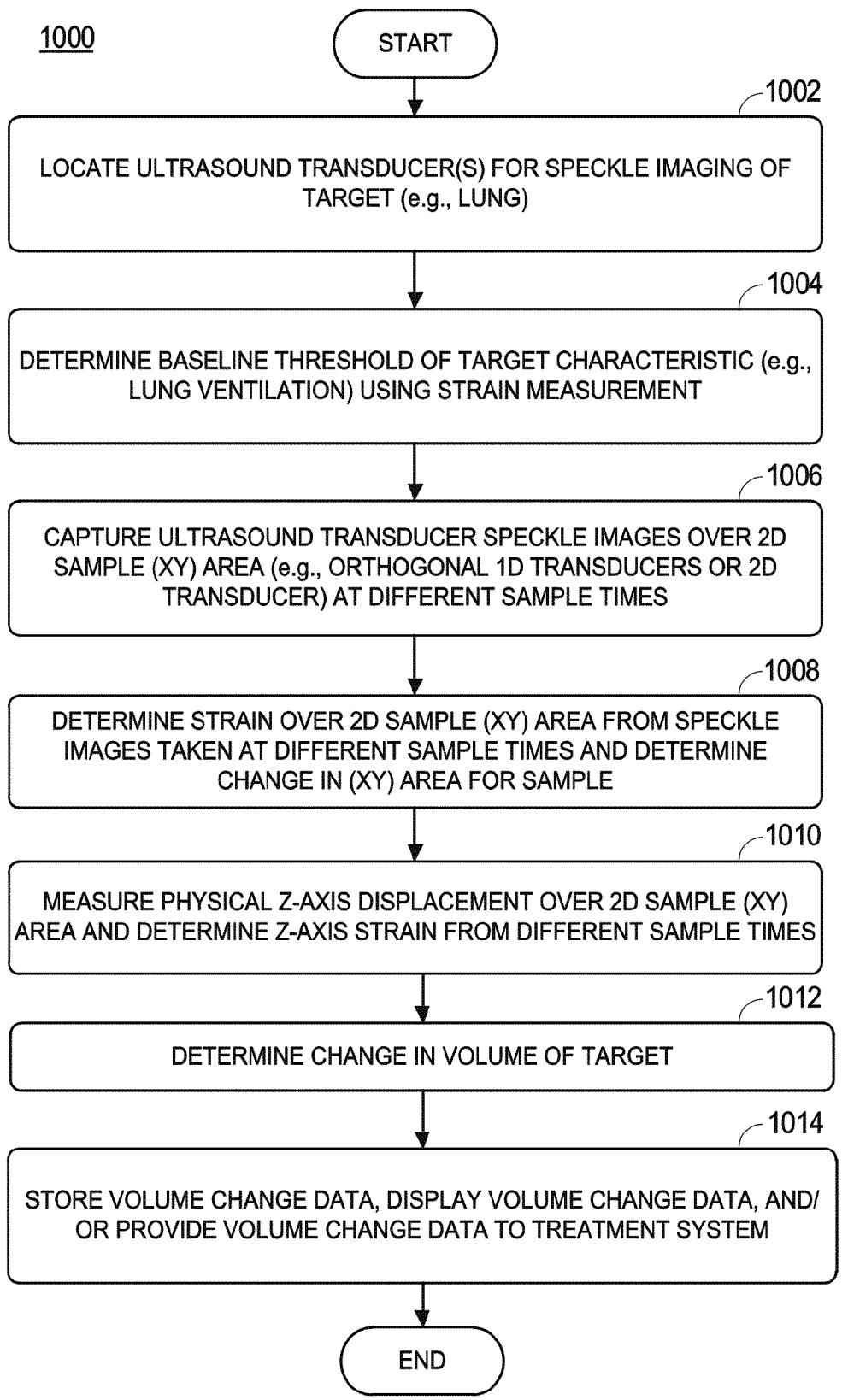
FIG. 3 is flow diagram of a process for determining lung volume change, in accordance with an example.

FIG. 3 illustrates an example process 1000 for determining changes in lung volume and as may be implemented in an imaging processing system, described further below. As noted the process 1000 may be implemented in whole or in part by any of the devices 100 and 200 and the computer 12. The process 1000, as described, determines strain, e.g., a local strain, from which lung volume change data may be determined. That local strain may be used in the determination of other characteristics of a target, as well, or as a proxy for lung volume.

Initially, at a block 1002, ultrasound transducers, either 2D array transducers or single 1D transducers, are positioned on a subject for image collection over a sample region. The transducers may be placed topically on the surface patient's skin, for example; although the particular techniques are not limited to a particular type of ultrasound image pickup. The particular locations of the transducers may also be determined based on the number of transducers being used to collect volumetric data, the size of the patient, the perceived size of the organ, the amount of intervening tissue between the upper skin surface and the lungs, and any prior information that might suggest variations in ventilation such as an underlying tumor, pneumonia, or atelectasis. Furthermore, the transducers are positioned for tracking, e.g., speckle tracking, in two orthogonal directions, such that the local strain can be determined from two-dimension tracking.

In some examples, the preferred locations of the ultrasound transducers may be determined from a 3D CT scan or other medical imaging modality, such as from a PET scanner, MRI, or etc. Indeed, in some applications it may be desirable, even with the cost effectiveness of the present techniques, to have simultaneous measurement of both ultrasound speckle images and other medical image data, for example to allow better registration of image data, more accurate and more developed tracking for treatment purposes, for example. Tracking may be assisted by the use of metallic markers visible in through both ultrasound and CT imaging systems, which may be used to register image data between the two modalities. Use of another medical imaging modality can also be used for calibrating the ultrasound system upon start up; although preferably ultrasound systems are calibrated at the factory or personalized, historical imaging data from the patient is used to determine optimum transducer location and operating thresholds.

At a block 1004, the imaging system determines thresholds for use in speckle tracking from the ultrasound images. For example, the block 1004 may set a threshold for backscattered signal strength, to be used in speckle tracking a comparison between two different ultrasound speckle images. Additionally, the mechanical index (MI) threshold for the ultrasound transducers may be provided at block 1004, where a range of MI<0.3 was chosen for some examples. While the actual MI values can vary, MI values or approximately 0.3 and below were chosen to prevent any chance of bioeffect especially given the neonatal population. Values for MI considerably below the 0.3 will be desired for numerous applications.

At a block 1006, ultrasound speckle images are captured over a sample area (see, e.g., FIG. 2 generally coinciding with a planar region across the xy-plane, and at different sampling times. The spacing between sampling times may be adjusted manually or may be determined automatically by the system. It is desired, in some examples, to collect speckle images at a full inspiration and then again at full expiration, to assess total lung volume changes. Thus, the block 1006 may collect speckle images at a sufficiently high frequency to identify, from the resulting data set, when the maximum and minimum lung volumes are achieved, and then identify these points amongst the image data stored from the captures overall. However, in other examples, real-time continuous capturing would be used.

At a block 1008, the process 1000 performs a strain determination, over the 2D sample area defined by the xy-area, based on the speckle image data collected from block 1006. This strain may be determined at each of a plurality of different sub-regions within the sample area, defined by the number of transducers and transducer spacing. The strain determinations of each of the sub-regions will then represent local ventilation at each of the sampled sites. The local strain at the lung surface is determined directly from 2D data taken by 2D ultrasound transducer arrays or from 1D transducer probes imaging along two orthogonal directions. In some examples, the strain data may be directly used to assess the condition of the target region, for example as a substitute indicator for lung volume changes. However, in the illustrated example, at the block 1008, the system may further determine from the strain values, a change in area of a two-dimensional area. For example, the block 1008 may determine an xy-plane change in area between two different speckle imaging time frames.

With strain determined over a two-dimensional area, a block 1010 now determines a physical displacement, along the z-axis, of the sample region at the different sample times corresponding to those of the block 1008. This may be done based on image data, as discussed. For example, the image processing system may define an osculating circle for the ultrasound images collected at each location of the ultrasound transducer to define a local curvature that changes from inspiration to expiration. By defining osculating circles at the surface and at inspiration and expiration, the image processor system may estimate a mean radius of these circles, where a change in radius of the mean radius will define a strain in the Z direction.

In other examples, the block 1010 collects data from an accelerator or other biometric sensor device and determines z-axis displacement.

The process 1000 will collect data over numerous cycles, via blocks 1004-1008, to help reduce variation and noise in data collection. The number of cycles can be set based on the number of transducers, the physiology of the patient, the need to avoid bioeffects, etc. In some examples, 10-20 cycles of data were collected at an MI<0.3, although higher MI values are contemplated. Furthermore, these blocks can perform statistically significant analyses on the collected data, to more accurately determine strain and the radii for osculating circles. Such statistically significant analysis may include averaging data, high and/or low threshold filtering, skewness analysis, kurtosis analysis, or a combination thereof.

At a block 1012, the system 1000 determines the change in volume between at least two different sample points, based on the xy-plane strain determination and the z-axis strain determination and applying Equations 1-3 above. The change may be stored in a database and provided to medical practitioners through a display, such as through the imaging processing system, or to an treatment system, such as a ventilator system, using a block 1014. In some examples, the ultrasound volume data may be displayed over an ultrasound image, for example by mapping approximate physical z-axis displacements onto an ultrasound image of the two-dimensional area for display. Such mapping could be achieved by overlaying a displacement vector, osculating circles, or other graphic to display z-axis displacement.

The process 1000 may be modified in various ways. For example, when using a 1D ultrasound transducer, even obtaining orthogonal data by rotating the scanhead 90° at each scanning site, the typical surface area insonified may be on the order of 2×2 cm. Because this may overestimate lung volume areas for neonates, the process can subsample smaller regions, as desired. Ultrasound access to the lung shouldn't be a problem, since we can easily scan between ribs. With a 2D array for the scanning, orthogonal samples may be acquired simultaneously, allowing faster, theoretically more accurate estimation of the radius of curvature changes from each orthogonal direction.

These measurements may be taken statically at full-inspiration and full-expiration, or at any two given speckle imaging times. However, the system may also be integrated with HFV ventilation treatments. In these examples, the block 1006 may receive a triggering signal from an HFV system, where that signal indicates the frequency or period of the ventilation treatment. In response, ultrasound speckle images may be synchronized (or clocked) with the timing of the HFV. Like the block 1006, the block 1010 may be triggered by a signal from an HFV system or other external ventilation system. Such triggering allows for more real-time assessment of lung ventilation and responsive to treatments, allowing medical personnel to more precisely know the ventilation distributions and measurement reproducibility throughout the lung for different tidal volumes. Examples ranges of detection are 30 Hz or lower, and in particular 15 Hz.

The accuracy of the volume change determination can be affected not only by the size and position of the osculating approximately circles, but by the number of such circles. When using multiple transducers simultaneously on a sample region, spacing the transducers too far apart, and the osculating circles will have larger gaps between them, leaving more of the lung to be approximated in volume change, but not actually measured. Although strain assessment over the entire 2D area may be achieved for these regions, exact approximation of the x-axis displacement will not be. Therefore, more transducers or denser or larger transducer arrays may be used, if desired, for more accurate measurement of displacement along the z-axis. Correlations between ultrasound speckle and osculating circles analysis and actual volumetric changes in the lung may be performed by comparing this data against CT, PET, MRI or other sample scan images, capable of volumetric analysis.

In some examples, other sensors could be used in addition to the ultrasound transducers and for the purposes of separately determining a z-axis displacement, either individually or in conjunction with the ultrasound transducers. For example, accelerometer sensors may be used with or within the ultrasound transducers to provide mapping of z-axis displacements over a respiratory cycle. The displacements could be measured, for example, from a mean position. Another sensor would be a mechanical displacement gauge with or within the ultrasound transducer to assist in calculation of the z-axis displacement.

Finally, binary measurements of expansion and contraction should still be correct even if the magnitudes are incorrect. Such measurements should distinguish areas of air trapping from truly ventilating lung. Thus if the underlying lung just translates, but the strain is zero, it is not being ventilated. This would correspond to air trapping.

The techniques herein may be used with any type of 1D or 2D ultrasound transducer. These include linear array and curved array transducers, steerable transducers, whether based on pulse wave or continuous wave Doppler, color Doppler, harmonic imaging, or any other ultrasound modality, preferably capable of producing speckle imaging. The technique could be used with 3D ultrasound devices, to determine approximating osculating circles, although 1D and 2D transducers generally should be more cost effective and more amenable to real time imaging.

Figure 4:
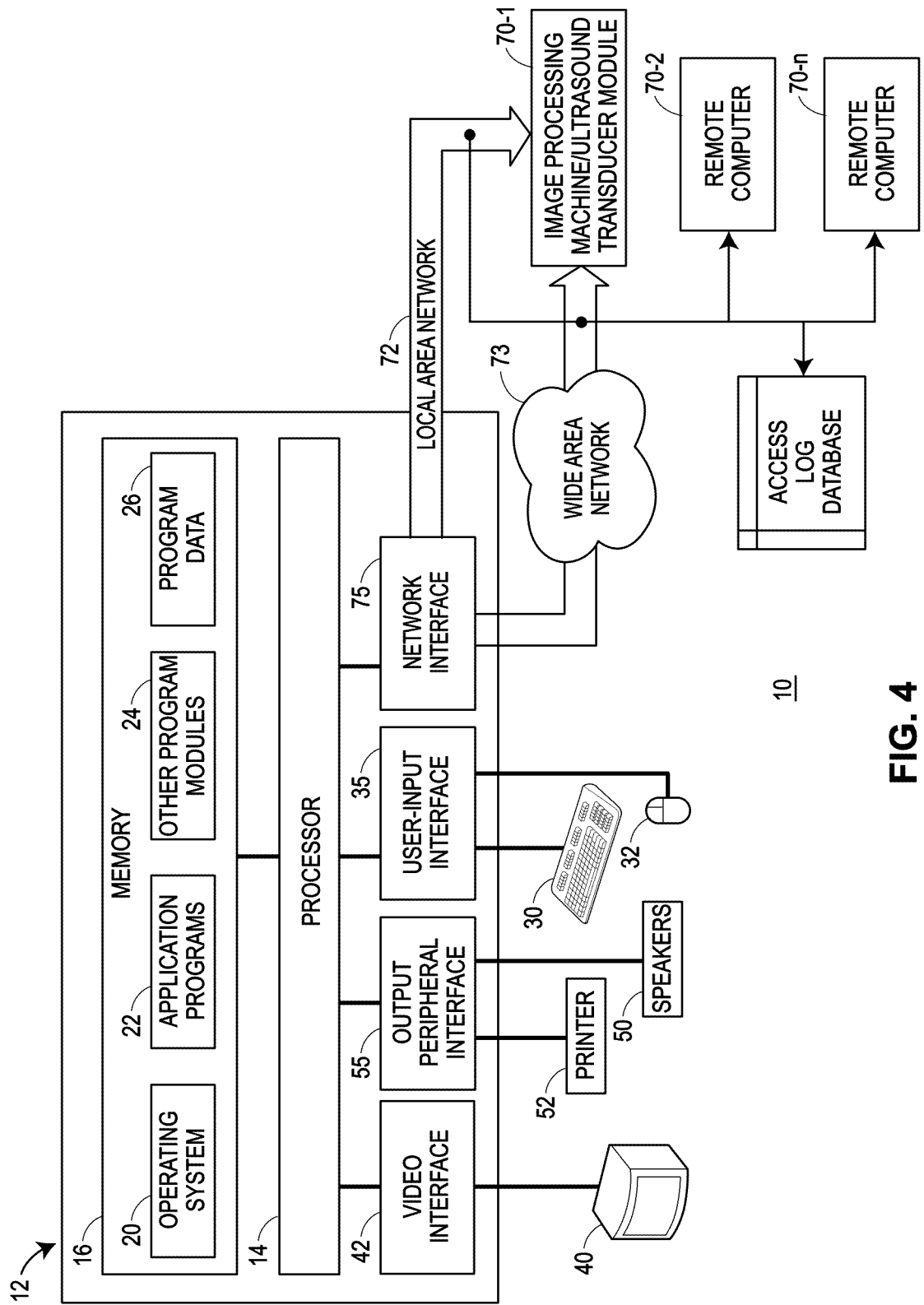
FIG. 4 illustrates an example lung volume analysis system, in accordance with an example.

FIG. 4 illustrates an example lung volume analysis system for performing a lung volume determination in accordance with the teachings hereinabove. The techniques described above may be coded, in software, hardware, firmware, or a combination thereof, for execution on a computing device such as that illustrated in FIG. 4. Generally, FIG. 4 illustrates an example of a suitable computing system environment 10 to interface with a medical professional or other user to analyze medical data, in particular ultrasound image data captured at the point of assessment or from a stored database of historical image data. It should be noted that the computing system environment 10 is only one example of a suitable computing environment and is not intended to suggest any limitation as to the scope of use or functionality of the method and apparatus of the claims.

An exemplary system for implementing the blocks of the method (FIG. 3) and apparatus includes a general-purpose computing device in the form of a computer 12. Components of computer 12 may include, but are not limited to, a processing unit 14 and a system memory 16. The computer 12 may operate in a networked environment using logical connections to one or more remote computers, such as remote computers 70-1, 70-2, . . . 70-n, via a local area network (LAN) 72 and/or a wide area network (WAN) 73 via a modem or other network interface 75. These remote computers 70 may include other computers like computer 12, but in some examples, these remote computers 70 include one or more of (i) a medical imaging system, (ii) a signal records database systems, (iii) a scanner, and/or (iv) a signal filtering system.

In the illustrated example, the computer 12 is connected to an image processing machine, labeled machine 70-1. The machine 70-1 may be a stand-alone ultrasound system, having ultrasound transducers (i.e., 2D arrays and/or 1D probes) and a processing machine for performing ultrasound imaging operation, including transmitting stimulation signals, collecting image data and z-axis displacement data, performing signal analysis on collected data, such as noise filtering, statistical analysis, etc., and storing (and/or buffering) that data and transmitting the same to the computer 12 for further analysis and strain and volume determination. In other examples, a series of ultrasound transducers may be connected directly to the computer 12, which would then control operation of the transducers, perform the data processing and storage functions, in place of the remote system 70-1.

Computer 12 typically includes a variety of computer readable media that may be any available media that may be accessed by computer 12 and includes both volatile and non-volatile media, removable and non-removable media. The system memory 16 includes computer storage media in the form of volatile and/or nonvolatile memory such as read only memory (ROM) and random access memory (RAM). The ROM may include a basic input/output system (BIOS). RAM typically contains data and/or program modules that include operating system 20, application programs 22, other program modules 24, and program data 26. These programs may include implementation of the blocks of process 1000. The computer 12 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 12 through input devices such as a keyboard 30 and pointing device 32, commonly referred to as a mouse, trackball or touch pad. Other input devices (not illustrated) may include a microphone, joystick, game pad, satellite dish, scanner, or the like. These and other input devices are often connected to the processing unit 14 through a user input interface 35 that is coupled to a system bus, but may be connected by other interface and bus structures, such as a parallel port, game port or a universal serial bus (USB). A monitor 40 or other type of display device may also be connected to the processor 14 via an interface, such as a video interface 42. In addition to the monitor, computers may also include other peripheral output devices such as speakers 50 and printer 52, which may be connected through an output peripheral interface 55.

Generally, the techniques herein may be coded in any computing language for execution on computer 12. Ultrasound speckle image data and z-axis displacement data may be obtained from the remote computers 70-1, 70-2, . . . 70-n and stored loaded on to any of the computer storage devices of computer 12. Once such data is obtained, a user may input or select the condition parameters through an input mechanism as described. Although, in other examples, the condition parameters may be pre-selected or automatically determined, for example, based on a particular type of analysis that is to be performed. The output of the executable program may be displayed on a display (e.g., a monitor 40), sent to a printer 52, stored for later use by the computer 12, or offloaded to another system, such as one of the remote computers 70. The output may be in the form of an image, a graph, a table or any combination thereof, by way of example. Operations of the system may be recorded in a log database for future reference as shown. This log database may be accessed at subsequent times.

The various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed:

1. An apparatus comprising:
    an imaging processing machine having a processor and a memory, wherein the processor is configured to execute instructions that when executed cause the imaging processing machine:
    to receive ultrasound images of a two-dimensional area corresponding to the target sample, where a first ultrasound image is taken at a first time period and a second ultrasound image is taken at a second time period after the first time period;
    to determine a change in strain value of the target sample over the two-dimensional area, wherein the strain value is determined from comparing the first ultrasound image to the second ultrasound image;
    to determine from the change in strain value, an xy-plane change in area of the target sample between the first time period and the second time period;
    to determine an approximate physical z-axis displacement over the two-dimensional area by approximating a change in local curvature of the two-dimensional area between the first time period and the second time period; and
    to determine a volume displacement of the target sample from the approximate physical z-axis displacement and the change in strain value.

2. The apparatus of claim 1, wherein the processor is further configured to execute instructions that when executed cause the imaging processing machine:
    to define at least one osculating circle at a region of the two-dimensional area of the target sample;
    to determine an initial radius of the at least one osculating circle at the first time period and a second radius of the at least one osculating circle at the second time period; and
    to determine the approximate physical z-axis displacement from a change between the initial radius and the second radius.

3. The apparatus of claim 2, wherein the processor is further configured to execute instructions that when executed cause the imaging processing machine:
    to define a plurality of osculating circles at for the two-dimensional area of the target sample;
    to determine for each of the osculating circles changes in radii between the first time period and the second time period; and
    to determine the approximate physical z-axis displacement as a mean of the determined changes in radii for the plurality of osculating circles.

4. The apparatus of claim 3, wherein the plurality of osculating circles have the same initial radius of curvature at the first time period.

5. The apparatus of claim 3, wherein at least some of the plurality of osculating circles have a different initial radius of curvature at the first time period.

6. The apparatus of claim 3, wherein osculating circles corresponding to a central region of the two-dimensional area have a larger initial radius of curvature than osculating circles corresponding to a peripheral region of the two-dimensional area.

7. The apparatus of claim 3, wherein the osculating circles are defined along two orthogonal directions of the two-dimensional area.

8. The apparatus of claim 3, wherein the processor is further configured to execute instructions that when executed cause the imaging processing machine to perform a statistically significant analysis of the determined changes in radii for the plurality of osculating circles to identify a subset of significance for the changes in radii, the method comprising determining the approximate physical z-axis displacement as mean of the subset of significance for the changes in radii.

9. The apparatus of claim 8, wherein the statistically significant analysis comprises a skewness analysis, kurtosis analysis, or a combination thereof.

10. The apparatus of claim 3, wherein the processor is further configured to execute instructions that when executed cause the imaging processing machine:
    to determine a plurality of approximate physical z-axis displacements over the two-dimensional area; and
    to map the plurality of approximate physical z-axis displacements onto an ultrasound image of the two-dimensional area for display.

11. The apparatus of claim 1, wherein the first ultrasound image and the second ultrasound image are speckle-containing images.

* * * * *